(12) United States Patent
Cheng et al.

(10) Patent No.: US 6,528,665 B1
(45) Date of Patent: Mar. 4, 2003

(54) PREVENTING UNDESIRED ODOR IN AND/OR PURIFYING ALKANEDIOLS

(75) Inventors: Chi Hung Cheng, Baton Rouge, LA (US); Gerald M. Sulzer, Baton Rouge, LA (US); John F. Balhoff, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 10/116,482

(22) Filed: Apr. 3, 2002

(51) Int. Cl.⁷ .................. C07D 301/32; C07D 301/12; C07C 27/06; C07C 29/159
(52) U.S. Cl. .................. 549/541; 549/523; 549/531; 549/542; 568/867; 568/868
(58) Field of Search ................. 549/541, 542, 549/531, 523; 568/867, 868

(56) References Cited

U.S. PATENT DOCUMENTS

| | | | |
|---|---|---|---|
| 2,833,788 A | 5/1958 | Skinner et al. | 260/348.5 |
| 3,644,497 A | 2/1972 | Mesich | 260/497 R |
| 3,708,506 A | 1/1973 | Brunie et al. | 260/348.5 L |
| 3,832,363 A | 8/1974 | Fetterly et al. | 260/348.5 V |
| 4,303,586 A | 12/1981 | Schirmann et al. | 260/348.31 |
| 4,303,587 A | 12/1981 | Schirmann et al. | 260/348.31 |
| 4,476,314 A | 10/1984 | Kuriyama et al. | 549/531 |
| 4,562,276 A | 12/1985 | Venturello et al. | 556/20 |
| 4,562,299 A | 12/1985 | Venturello et al. | 568/811 |
| 4,595,671 A | 6/1986 | Venturello et al. | 502/159 |
| 5,274,140 A | 12/1993 | Venturello et al. | 549/531 |
| 5,324,849 A | 6/1994 | Bonsignore et al. | 556/14 |
| 5,344,946 A | 9/1994 | Warwel et al. | 549/531 |
| 5,780,655 A | 7/1998 | Shum | 549/531 |
| 6,051,725 A | 4/2000 | Crivello et al. | 549/524 |

OTHER PUBLICATIONS

Abstract of DE 19929196, issued Dec. 2000, from Espa@cenet.

Hori et al., "Synthetic Applications of Arylselenenic and Arylseleninic Acids, Conversion of Olefins to Allylic Alcohols and Epoxides", J. Org. Chem, vol. 43, No. 9, 1978, pp. 1689–1697.

Payne et al., "Reactions of Hydrogen Peroxide. IV. Sodium Tungstate Catalyzed Epoxidation of a,b–Unsaturated Acids", J. Org. Chem., 1959, vol. 24, pp. 54–55.

Venturello et al., "A New, Effective Catalytic System for Epoxidation of Olefins by Hydrogen Peroxide Under Phase–Transfer Conditions", J. Org. Chem., 1983, vol. 48, No. 21, pp. 3831–3833.

Venturello et al., "Quaternary Ammonium Tetrakis(diperoxotungsto)phosphates(3–)as a New Class of Catalysts for Efficient Alkene Epoxidation with Hydrogen Peroxide", J. Org. Chem., 1988, vol. 53, No. 7, pp. 1553–1557.

Venturello et al., "A Convenient Catalytic Method for the Dihydroxylation of Alkenes by Hydrogen Peroxide", Communications, 1989, pp. 295–297.

*Primary Examiner*—Ba K. Trinh
(74) *Attorney, Agent, or Firm*—E. E. Spielman, Jr.

(57) ABSTRACT

Epoxyalkanes are subjected to at least one of the following washing operations: (1) washing with aqueous inorganic base, and then with aqueous borohydride, or vice versa; or (2) washing with an aqueous solution of both inorganic base and borohydride. Undesirable odor is reduced or eliminated from alkanediol(s), if produced from the treated epoxyalkane(s) by hydrolysis. Use of such washing procedures in the production of alkanediols is also described.

37 Claims, 3 Drawing Sheets

Figure 1. Continuous Reaction/Distillation System

Figure 2. Batch Reactor System

Figure 3. Nitrogen Stripping Column

PREVENTING UNDESIRED ODOR IN AND/OR PURIFYING ALKANEDIOLS

BACKGROUND

Alkanediols, especially vicinal alkanediols, such as 1,2-alkanediols, 2,3-alkanediols, 3,4-alkanediols, and their higher homologs, are typically produced by hydrolysis of epoxyalkanes. For certain commercial applications the alkanediol must meet stringent low odor specifications.

A practical commercial method for producing the epoxyalkane starting materials involves reaction of an alkene with hydrogen peroxide in the presence of a heavy metal catalyst system, such as a tungsten-based catalyst. While effective, such processes can produce small amounts of coproducts as impurities. Unless removed trace amounts of such impurities tend to produce commercially unacceptable odors in the alkanediols produced therefrom. A case in point is 1,2-hexanediol, a commercially important product for which there is a stringent odor specification which must be satisfied.

While it is possible to purify epoxyalkanes by distillation, this necessitates in commercial practice use of an expensive distillation operation involving use of expensive distillation equipment. A need thus exists for a simpler and more economical way, compared to expensive distillation, of removing the odor components and/or their precursors so that the final alkanediol product has reduced odor characteristics, and enabling the product to meet odor specifications which maybe applicable to the product. It would be particularly desirable if a chemical treatment method could be found for fulfilling this need without adversely affecting the product or materially reducing the yield of the finished product.

This invention is deemed to fulfill the foregoing need in a highly effective manner.

BRIEF SUMMARY OF THE INVENTION

This invention provides commercially attractive ways of preventing undesired odors in alkanediols, especially alkanediols produced from epoxyalkanes, and most especially in vicinal alkanediols such as 1,2-alkanediols formed from corresponding vicinal epoxyalkanes such as 1,2-epoxyalkanes. In addition, this invention makes it possible to provide commercially attractive ways of purifying epoxyalkanes including those intended for use as raw materials in the synthesis of alkanediols.

Among the various embodiments of this invention is a process of treating at least one epoxyalkane such that if the epoxyalkane is hydrolyzed to form at least one alkanediol, undesirable odor in the resultant alkanediol is reduced or eliminated. The process comprises subjecting the epoxyalkane(s) to at least one of the following washing operations:

(i) washing the epoxyalkane(s) at least once with an aqueous washing solution of inorganic base, and then washing the epoxyalkane(s) at least once with an aqueous washing solution of borohydride; or (ii) washing the epoxyalkane(s) at least once with an aqueous washing solution of borohydride, and then washing the epoxyalkane(s) at least once with an aqueous washing solution of inorganic base; or (iii) washing the epoxyalkane(s) at least once with an aqueous washing solution of both inorganic base and borohydride;

such that undesirable odor is reduced or eliminated from alkanediol(s), if produced from the treated epoxyalkane(s) by hydrolysis. In washing operations (i) and (ii) at least two aqueous washes are carried out, one of which is conducted using an aqueous solution of an inorganic base, and the other of which is conducted using an aqueous solution of a water-soluble borohydride reagent. These aqueous washes can be carried out in either order, and of course, more than one wash with an aqueous inorganic base and/or more than one wash with an aqueous water-soluble borohydride can be utilized.

In washing operation (iii), the inorganic base and the borohydride are combined in the same aqueous solution and utilized in the washing procedure. This simplifies the overall operation and involves less time in conducting the operation. Accordingly, washing operation (iii) is preferred. It will be appreciated that, if necessary or desired, more than one wash with the aqueous alkaline solution of borohydride and inorganic base can be used. Also if necessary or desired, one or more washes with either an aqueous inorganic base or an aqueous solution of a water-soluble borohydride can be utilized before and/or after carrying out one wash, or two or more consecutive washes, with the aqueous alkaline solution of borohydride and inorganic base.

Another embodiment is a process for producing an alkanediol with reduced or eliminated undesirable odor or odor-causing impurities, which process comprises:

a) conducting at least one of the following washing operations on at least one epoxyalkane:
   (i) washing the epoxyalkane(s) at least once with an aqueous washing solution of inorganic base, and then washing the epoxyalkane(s) at least once with an aqueous washing solution of borohydride; or
   (ii) washing t he epoxyalkane(s) at least once with an aqueous washing solution of borohydride, an d then washing the epoxyalkane(s) at least once with an aqueous washing solution of inorganic base; or
   (iii) washing the epoxyalkane(s) at least once with an aqueous washing solution of both inorganic base and borohydride; and
   separating the epoxyalkane(s) from the aqueous washing solution or solutions used; and b) hydrolyzing in the presence of acid or bas e at least one epoxyalkane from a) to form at least one alkanediol.

Still another embodiment is a process of producing an alkanediol, which process comprises:

A) epoxidizing in a liquid phase, an epoxidizable olefinic compound with hydrogen peroxide in the presence of a catalytic quantity of a tungsten-containing catalyst, to form an epoxide;

B) conducting at least one of the following washing operations on said epoxide:
   (i) washing said epoxide at least once with an aqueous washing solution of inorganic base, and then washing said epoxide at least once with an aqueous washing solution of borohydride; or
   (ii) washing said epoxide at least once with an aqueous washing solution of borohydride, and then washing said epoxide at least once with an aqueous washing solution of inorganic base; or
   (iii) washing said epoxide at least once with an aqueous washing solution of both inorganic base and borohydride; and
   separating the epoxide from the aqueous washing solution or solutions used; and C) hydrolyzing in the presence of acid or base th e epoxide from B) to form alkanediol.

These and other embodiments, features, and advantages of this invention will become still further apparent from the ensuing description, accompanying drawings, and appended claims.

FURTHER DETAILED DESCRIPTION OF THE INVENTION

Treatment of Epoxyalkanes

Any epoxyalkane requiring purification (e.g., an epoxyalkane product containing aldehyde, ketone, and/or carboxylic acid impurities) can be subjected to a purification process of this invention, even apart from whether odor of the product is a consideration. Epoxyalkanes which can be treated pursuant to this invention include the vicinal epoxyalkanes (i.e., alkanes in which an oxygen atom is bonded to each of two adjacent carbon atoms), which are sometimes referred to as 1,2-epoxides, and non-vicinal epoxyalkanes (i.e., alkanes in which an oxygen atom is bonded to each of two carbon atoms separated by an intervening carbon atom), which are sometimes referred to as 1,3-epoxides. Compounds of either type type having in the range of 2 to about 12 carbon atoms in the molecule can be treated. This invention is preferably applied to vicinal epoxyalkanes having at least about 5 carbon atoms in the molecule. Typically the vicinal epoxyalkanes treated pursuant to this invention will contain up to about 8 carbon atoms per molecule, although even higher members of this series can be treated, if desired. The alkane backbone can be branched but preferably the epoxyalkane is a derivative of a straight chain (linear) hydrocarbon. The epoxy group of the vicinal epoxyalkanes can be in the 1,2-position, or in an internal position such as the 2,3-, or 3,4-positions. The 1,3-epoxides which can be treated are exemplified by 1,3-trimethylene oxide, 1-methyl-1,3-trimethylene oxide, and 1,3-diethyl-1,3-trimethylene oxide. Non-limiting examples of vicinal epoxyalkanes which can be treated include such compounds as 1,2-epoxyethane (ethylene oxide), 1,2-epoxypropane, 1,2-epoxybutane, 2,3-epoxybutane, 1,2-epoxypentane, 2,3-epoxypentane, 1,2-epoxyhexane, 2,3-epoxyhexane, 3,4-epoxyhexane, 1,2-epoxy-2-methylbutane, 1,2-epoxy-3-methylbutane, 1,2-epoxy-4-methylpentane, 1,2-epoxy-3-ethylhexane, 1,2-epoxy-5,5-dimethylhexane, 2,3-epoxy-5,6-dimethyloctane, 1,2-epoxynonane, 1,2-epoxydodecane, and analogous compounds. Preferred epoxides are the linear compounds 1,2-epoxypentane, 1,2-epoxyhexane, 1,2-epoxyheptane, and 1,2-epoxyoctane. The invention can be applied to mixtures of two or more different epoxyalkanes, but preferably is applied to purification of a single epoxyalkane. Most preferred is treatment of 1,2-epoxyhexane because of its use in forming 1,2-hexanediol, a product having a stringent odor specification. Similar odor specifications or requirements could very well be applicable to homologous compounds such as 1,2-epoxypentane, 1,2-epoxyheptane and 1,2-epoxyoctane, as well as internal epoxy analogs or branched chain analogs of any or all such compounds.

The treatment of epoxyalkanes pursuant to this invention involves washing one or a mixture of such compounds (1) in any sequence with at least one aqueous solution of an inorganic base and separately with at least one aqueous solution of a water-soluble borohydride, or preferably (2) with at least one aqueous alkaline solution of both borohydride and inorganic base, and separating the washed epoxyalkane from the one or more washing solutions used. Bases useful in forming such aqueous treating solutions include alkali metal bases, alkaline earth metal bases, and bases of other appropriate cations such as ammonium or zinc. A few non-limiting examples of suitable bases include, for example, sodium carbonate, sodium oxide, sodium hydroxide, sodium hydride, potassium carbonate, potassium oxide, potassium hydroxide, potassium hydride, zinc hydroxide, and corresponding derivatives of lithium, magnesium, and calcium. Alkali metal bases are preferred; more preferred are alkali metal hydroxides, and sodium hydroxide is most preferred as the inorganic base. Mixtures of inorganic bases can be used. The inorganic base may be introduced to the reaction vessel in solid form or as a solution; use of an aqueous solution of the inorganic base is particularly preferred. When an aqueous solution of inorganic base is used, the concentration of inorganic base in the aqueous solution is preferably in the range of about 2 wt % to about 50 wt %.

Any inorganic borohydride can be used in forming the treating solutions, whether used alone or in combination with an inorganic base. A few non-limiting examples of borohydride sources include such borohydrides as lithium borohydride, sodium borohydride, potassium borohydride, calcium borohydride, and aluminum borohydride. Because of its greater availability, sodium borohydride is usually preferred for use.

Sodium borohydride ($NaBH_4$) in caustic solution, which is readily available commercially, is a preferred treating agent. Such a solution has been found to effectively convert aldehyde impurities (e.g., pentanal) and ketone impurities (e.g., 1-hydroxy-2-hexanone) to alcohols (e.g., pentanol, 1,2-hexanediol) and acid impurities (e.g., pentanoic acid) to organic salts (e.g., sodium pentanoic acid). Pursuant to this invention, treated epoxyalkanes especially vicinal epoxyalkanes (e.g., 1,2-epoxyhexane) can be hydrolyzed under acid or base conditions to the corresponding alkanediol (e.g., 1,2-hexanediol), products which are much purer and which typically have much less odor as compared to the product produced from same epoxyalkane treated with aqueous caustic only.

The epoxyalkane to be purified can be from a crude reaction mixture or can be prepurified (i.e., already purified via another method) prior to the use of the purification process of this invention. Preferably, however, the purification process of this invention is conducted on the crude reaction mixture which has not been previously purified, as this is a more efficient way to operate.

As noted above, numerous variations are available for use in carrying out the washing step(s) of this invention. The fundamental requirement is that the epoxide be contacted with an aqueous solution of a water-soluble inorganic base and an aqueous solution of a water-soluble borohydride, which can be two separate solutions used in either order, or preferably which is a single solution of both the water-soluble inorganic base and the water-soluble borohydride. If desired, further washes with aqueous inorganic base and/or aqueous water-soluble borohydride reagent can be used, and when a wash with the combination of a water-soluble and an inorganic base and a water-soluble borohydride reagent is utilized, these further washes can precede or follow the washing with such combination. It is also possible to carry out a series of two or more consecutive washing steps with an aqueous solution of both an inorganic base and a water-soluble borohydride reagent. Here again, before or after, or both before and after, carrying out such consecutive washing steps, one or more washings with either an aqueous solution of an inorganic base or an aqueous solution of a water-soluble borohydride reagent (or each such solution seriatim in either order) can be used.

When more than one washing operation in accordance with this invention is used, the washed epoxyalkane can be separated from each washing solution used. This is generally the preferred mode of operation. However, more than one washing operation can be carried out before separating the washed epoxyalkane from the resultant washing solution. For example, in a suitably large washing vessel containing epoxyalkane to be washed, an initial quantity of a solution of, say, sodium hydroxide can be added and mixed with the epoxyalkane. Then without effecting a separation, a quantity of a solution of sodium borohydride can be added and mixed with the contents of the vessel including the epoxyalkane. After such second washing, the phases can be allowed to separate and a phase cut carried out in order to separate the aqueous and organic phases from each other.

In conducting the purification of one or more epoxyalkanes in a preferred manner, at least one inorganic base, at least one borohydride source, and at least one 1,2-epoxyalkane are mixed together. These ingredients can be mixed together in any order. It is preferred to use the inorganic base as an aqueous solution. Also preferred is the use of the borohydride source as an aqueous solution. Most preferred is a single aqueous solution of both the inorganic base and the borohydride source, which is then mixed with the epoxyalkane. The treatment can be conducted at ambient temperature or at moderately elevated temperature, preferably at 5–60° C.

The duration of the washing step (or each washing step when a plurality of washing steps are used) is typically 0.5–30 minutes, dependent somewhat on the reactivity of the epoxyalkane, the mixing efficiency, the temperature, and the concentrations of the borohydride and base used (whether separately or in combination). The amount of washing solution(s) used should of course be sufficient to purify or to remove and/or change a sufficient amount of impurities to achieve the desired purity or odor requirements. A few pilot experiments will suffice in any case where optimum washing conditions have not already been established. Any washing step utilized in the practice of this invention can be followed by one or more washes with water, if desired. Thus, a preferred wash using an aqueous alkaline borohydride solution can be followed by one or more water washes or extractions with water, if desired. Whether or not a water wash is used, the treated product mixture can then be distilled, if desired. In preferred operations, the treated product mixture, with or without one or more final water washes, is subjected to stripping in a stripping column operated with an inert stripping gas such as nitrogen.

Epoxyalkanes which can be treated pursuant to this invention can be produced by various processes. Thus the epoxyalkane can be formed, for example, by reaction of alkali with 1,2-chlorohydrins, or by reaction of alkene with peroxyacids. Also alkenes can be oxidized to their respective epoxides with hydrogen peroxide in the presence of certain metal catalysts, such as a peroxotungstate catalyst, as described for example in U.S. Pat. Nos. 5,274,140 to Venturello et al., and 5,780,655 to Shum. A few other references of interest in this connection are Venturello et al., *J. Org. Chem.* 1983, 48, 3831; Payne et al., *J. Org. Chem.* 1959, 24, 54; Hori et al., id., 1978 43, 1689; and Pralus et al., *Fundamental Research in Homogeneous Catalysis*, M. Tsutsui, ed., Plenum, N.Y., 1979, Vol. 3, pp. 327–343 and references therein.

Processes of Preparing and Treating Epoxyalkanes

A number of embodiments of this invention involve forming an epoxide by a process which comprises epoxidizing in the liquid phase, an olefinic compound (preferably an alkene), with hydrogen peroxide in the presence of a catalytic quantity of a tungsten-based catalyst system (preferably a peroxotungstate catalyst system), and washing product mixture so-formed (i) in any sequence with at least one aqueous alkaline solution of an inorganic base and separately with at least one aqueous solution of a water-soluble borohydride, or preferably (ii) with at least one aqueous alkaline solution of borohydride and inorganic base (i.e., where both the inorganic base and a water-soluble borohydride are used in forming the same washing solution). In a preferred embodiment, (a) boric acid and (b) at least one alkanediol individually and/or as a reaction product of (a) and (b) are included in the liquid phase of the liquid phase catalytic epoxidation step. In a further preferred embodiment the resultant aqueous solution and the washed epoxyalkane are separated from each other, and the separated epoxyalkane is hydrolyzed in the presence of acid or base to form alkanediol.

Another preferred embodiment is a process of forming an epoxide by a process which comprises:

A) continuously or substantially continuously feeding aqueous hydrogen peroxide solution into a reaction mixture formed from components comprising at least one olefinic hydrocarbon (preferably a 1-alkene) to which have been added (i) tungstic acid and/or a tungsten compound, preferably a tungsten (VI) compound, and an inorganic acid, (ii) an onium compound, preferably a quaternary ammonium compound, (iii) boric acid and (iv) at least one alkanediol and/or (v) a borate ester-containing mixture formed from boric acid and at least one alkanediol;

B) continuously or substantially continuously removing water from the reaction mixture by distillation so that at least during substantially the entire time the aqueous hydrogen peroxide is being fed, the reaction mixture has a liquid phase which is a single liquid phase or an essentially single liquid phase whereby an epoxide product is formed; and C) subjecting epoxide product from B) to at least one of the following washing operations:
  (i) washing the epoxide product at least once with an aqueous washing solution of inorganic base, and then washing the epoxide product at least once with an aqueous washing solution of borohydride; or
  (ii) washing the epoxide product at least once with an aqueous washing solution of borohydride, and then washing the epoxide product at least once with an aqueous washing solution of inorganic base; or
  (iii) washing the epoxide product at least once with an aqueous washing solution of both inorganic base and borohydride.

In a further preferred embodiment the olefinic hydrocarbon is a linear olefin, preferably a 1-alkene, and the resultant aqueous solution and the washed epoxide product from C) are separated from each other, and the separated epoxide product is hydrolyzed in the presence of acid or base to form alkanediol, preferably 1,2-alkanediol.

Still another preferred embodiment is a process of forming an epoxide, which process comprises:

A) continuously cofeeding (1) aqueous hydrogen peroxide solution and (2) at least one olefinic hydrocarbon, into a reaction mixture formed from components comprising (a) at least one olefmic hydrocarbon (b) a tungsten compound, preferably (i) tungstic acid and/or (ii) a tungsten (VI) compound and an inorganic acid, (c) an onium compound, preferably a quaternary ammonium compound, and (d) boric acid and (e) at least one alkanediol and/or (f) a borate ester-containing mixture formed from boric acid and at least one alkanediol, such that at least one epoxide is continuously being formed;

B) continuously or substantially continuously removing water from the reaction mixture by distillation so that at least during substantially the entire time the aqueous hydrogen peroxide is being fed, the reaction mixture has a liquid phase which is a single liquid phase or an essentially single liquid phase whereby an epoxide product is formed; and C) subjecting epoxide product from B) to at least one of the following washing operations:
   (i) washing the epoxide product at least once with an aqueous washing solution of inorganic base, and then washing the epoxide product at least once with an aqueous washing solution of borohydride; or
   (ii) washing the epoxide product at least once with an aqueous washing solution of borohydride, and then washing the epoxide product at least once with an aqueous washing solution of inorganic base; or
   (iii) washing the epoxide product at least once with an aqueous washing solution of both inorganic base and borohydride.

In a further preferred embodiment the olefinic hydrocarbon is a linear olefin, preferably a 1-alkene, and the resultant aqueous solution and the washed epoxide product from C) are separated from each other, and the separated epoxide product is hydrolyzed in the presence of acid or base to form alkanediol, preferably 1,2-alkanediol.

The formation of epoxides as above wherein (a) boric acid and (b) at least one alkanediol individually and/or as a reaction product of (a) and (b) are included in the liquid phase of the liquid phase catalytic epoxidation step forms the subject of commonly-owned copending application Ser. No. 10/116,508, filed Apr. 03, 2002.

In the embodiments of this invention in which the epoxyalkane is being prepared as above, and then subjected to further treatments, the process steps for making the epoxyalkane comprise mixing hydrogen peroxide, preferably in the form of a concentrated aqueous hydrogen peroxide solution, with at least one olefinic hydrocarbon, preferably a 1-alkene, in the presence of a novel tungsten-based catalyst system in an essentially single phase liquid reaction mixture. The novel tungsten-based catalyst system is either preformed or formed in situ by mixing together a tungsten compound (preferably a tungsten (VI) compound), an inorganic acid, an onium compound (preferably a quaternary ammonium salt), boric acid, an alkanediol, and hydrogen peroxide. Instead of (or in addition to) using a tungsten (VI) compound and an inorganic acid, tungstic acid can be used. Also, the boric acid and alkanediol can be premixed whereby one or more borate esters are formed. In either case, the catalyst system, whatever its actual composition may be, is present in the liquid phase reaction mixture prior to or shortly after initiating the feed of hydrogen peroxide. Before and during the epoxidation reaction, water is continuously or substantially continuously removed from the reaction mixture by distillation so that an essentially single-phase liquid reaction mixture is maintained during the reaction. Preferably, the alkanediol used in forming the catalyst is a 1,2-alkanediol, most preferably 1,2-hexanediol. In a preferred embodiment wherein an onium compound is used, the onium compound is a quaternary ammonium salt in which at least one of the substituents on the nitrogen atom is an alkyl group containing at least six carbon atoms.

Preferably, the epoxyalkane is formed using a continuous epoxidation process which comprises concurrently, or substantially concurrently, feeding into a reaction zone containing a tungsten-based catalyst system, as described above, (A) hydrogen peroxide, preferably in the form of concentrated aqueous hydrogen peroxide solution, and (B) at least one olefinic hydrocarbon, preferably a 1-alkene. During all or substantially all of the time the feeding of (A) and (B) is occurring, the reaction zone is maintained under reflux conditions, such that water, epoxide product, unreacted olefinic hydrocarbon, and some reaction byproducts are continuously or substantially continuously removed from the reaction zone in the form of a vapor stream. The epoxide can be recovered in different ways. In one embodiment, the organic phase is separated from the water phase of the condensed vapor stream, and the epoxide is distilled from the organic phase, by batch or continuous distillation. The olefinic hydrocarbon is isolated and returned to the reaction zone. In another embodiment, which is preferred, the epoxide is recovered by feeding the vapor stream to a distillation column, where the overhead distillate is composed of the olefinic hydrocarbon and water. The olefinic hydrocarbon is separated from the water by means of a liquid-liquid phase separation, and is returned to the reaction zone. The epoxide is recovered as bottoms from the distillation column. This latter recovery procedure is preferred because it eliminates the need to condense the epoxide before its final separation and thus is less energy-intensive, and requires lower capital and operating costs.

The chemical composition of the novel tungsten-based catalyst systems in which (i) boric acid and (ii) at least one alkanediol individually and/or as a reaction product of (i) and (ii) are included in the liquid phase of the liquid phase catalytic epoxidation step is not known. What is known however is that whatever the actual composition may be, the composition is very effective as an epoxidation catalyst. Moreover such inclusion of (i) and (ii) makes it possible to provide catalyst systems that retain their effectiveness for extended periods of time.

A variety of tungsten-based epoxidation catalysts can be used in forming these catalyst systems. These tungsten-based epoxidation catalysts include those described for example in U.S. Pat. Nos. 5,274,140; 5,324,849; or 5,780,655, the full disclosures of which are incorporated herein by reference. These catalysts are improved by including or using therewith boric acid and alkanediol and/or a boric acid ester composition formed from boric acid and alkanediol. Other catalyst systems which can be used in this manner are the tungsten-based catalysts containing phosphorus or arsenic that are described by Venturello and coworkers in various references such as U.S. Pat. No. 4,562,276; U.S. Pat. No. 4,562,299; *J. Org. Chem*, 1983, 48, 3831-3; and *J. Org. Chem.*, 1988, 53, 1553-7, the full disclosures of which are incorporated herein by reference, and with which are included or used boric acid and alkanediol and/or a boric acid ester composition formed from boric acid and alkanediol. These latter patents refer to such precursor catalyst (of course in the absence of the boric acid and alkanediol and/or a boric acid ester composition formed from boric acid and alkanediol) by the formula $$Q_3XW_4O_{24-2n}$$

where Q is an onium $(RR_1R_2R_3M)^{\oplus}$ cation in which M is chosen from amongst N, P, As, and Sb, and R, $R_1$, $R_2$, and $R_3$ are the same or different, and represent hydrogen atoms or hydrocarbon groups having a total of from 20 to 70 carbon atoms; X is an atom of P or As; and n is an integer from amongst 0, 1 and 2.

It appears that the nomenclature used in describing the known precursor tungsten-based catalysts in the foregoing references is not uniform or standardized. Nevertheless without desiring to be bound by theory it appears reasonable to consider that these precursor catalyst components when used with peroxide yield peroxotungsto or peroxotungstate catalysts which typically include phosphorus, arsenic, antimony, or ammonium species. Thus for convenience the tungsten-based catalysts are sometimes referred to collectively herein as peroxotungstate catalysts, and the catalysts which are formed by modifying or improving the known peroxotungstate catalysts by inclusion or use therewith of boric acid and an alkanediol, and/or a boric acid ester composition formed from boric acid and alkanediol, are sometimes referred to collectively herein as the boron-modified catalysts.

A variety of tungsten compounds can be used in making the peroxotungstate catalysts and the boron-modified catalysts, such as for example, $WO_2$, $W_2O_5$, $WO_3$, $WS_2$, $WS_3$, $WCl_2$, $WCl_4$, $WCl_5$, $WCl_6$, $WBr_2$, $WBr_5$, $WBr_6$, $WI_2$, $WI_4$, $WOCl_4$, $WO_2Cl_2$, $WOBr_4$, $WO_2Br_2$, $W(CO)_6$, and the like. Preferred are tungsten (VI) compounds, especially salts of tungstate ($WO_4^{2-}$). Examples of suitable tungstate salts include but are not limited to lithium tungstate, sodium tungstate, potassium tungstate, cesium tungstate, magnesium tungstate, calcium tungstate, barium tungstate, ammonium tungstate, cadmium tungstate, cerium tungstate, cobalt tungstate, copper tungstate, and silver tungstate. Preferred tungstate salts are alkali metal tungstates and alkaline earth tungstates. Highly preferred tungstates are sodium tungstate and potassium tungstate. Mixtures of such tungstates can be used. Inorganic acid is typically added to convert the tungstate salt to its acid form. The amount of acid used is somewhat dependent on the nature of the tungstate salt chosen. It is sometimes advantageous to use slightly excess acid. For example, when sulfuric acid and sodium tungstate are used, the mole ratio of the acid to tungstate is preferably in the range of about 1:1 to about 1:3. Other inorganic acids suitable for use include, but are not limited to, sulfurous acid, nitric acid, nitrous acid, phosphoric acid, hydrochloric acid, hydrobromic acid, and hydroiodic acid. More than one aqueous inorganic acid may be used in making the preformed catalyst solution.

Sources of phosphorus or antimony that, optionally, can be used in forming tungsten-based catalyst precursors include $P_2O_5$, $As_2O_5$, $PCl_5$, $AsCl_5$, $POCl_3$, $AsOCl_3$, or polyphosphoric acid, or water-soluble salts containing P and W or As and W, such as salts of phosphotungstic acid or arsenotungstic acids. Preferably an onium compound is used in forming these catalyst systems. Suitable onium compounds are quaternary salts of the formula:

$$(R_1R_2R_3R_4)^{\oplus}X^{\ominus}$$

Where M is N, P, As, or Sb; X is a stable inorganic anion such as $Cl^{\ominus}$, $HSO_4^{\ominus}$, $NO_3^{\ominus}$, etc.; and $R_1$, $R_2$, $R_3$, and $R_4$ are, independently, hydrogen atoms or hydrocarbyl groups providing a total number of carbon atoms of up to about 70, and preferably in the range of about 8 to about 50, and more preferably in the range of about 18 to about 50 carbon atoms. Most preferred as a group are the quaternary ammonium compounds, and of these quaternary ammonium salts in which at least one of the hydrocarbyl substituents on the nitrogen atom contains at least six carbon atoms are preferred. More preferably, three of the substituents on the nitrogen atom contain at least six carbon atoms per substituent; still more preferably, each of the three substituents contains 6 to about 16 carbon atoms, and the remaining substituent is ethyl, or more preferably methyl. Tetraalkylammonium compounds having one methyl or ethyl group and three alkyl groups which contain, independently, in the range of 6 to about 12 carbon atoms are another preferred group. Especially preferred are tetraalkylammonium halides in which two or three of the alkyl groups substituents on the nitrogen atom each contain independently in the range of 6 to about 12 carbon atoms and each of the one or two other alkyl substituents on the nitrogen atom is independently a methyl or ethyl group. The anion portion of the quaternary ammonium salt can be any of a number of inorganic anions, including nitrate, nitrite, borate, chloride, bromide, and iodide. Chloride and bromide are preferred inorganic anions; thus, the quaternary ammonium salt is preferably a chloride or bromide salt. Examples of quaternary ammonium salts that can be used include, but are not limited to, hexyltrimethylammonium chloride, dihexyldimethylammonium bromide, hexyloctyldiethylammonium chloride, dihexyloctylmethylammonium chloride, trioctylethylammonium bromide, tricaprylylmethylammonium chloride, and tridodecylmethylammonium bromide. Preferred quaternary ammonium salts are such tetraalkylammonium halides as methyl(tri-n-octyl)ammonium chloride, methyl(tri-n-octyl) ammonium bromide, ethyl(tri-n-octyl)ammonium chloride, ethyl(tri-n-octyl)ammonium bromide, di(hexyl)(octyl)methylammonium chloride, di(hexyl)(octyl)methylammonium bromide, tri(dodecyl)methylammonium chloride, or tri(dodecyl)methylammonium bromide. Mixtures of quaternary ammonium salts can be used. The mole ratio of the ammonium salt to tungstate salt is preferably in the range of about 0.5:1 to about 1.5:1, and more preferably in the range of about 0.8:1 to about 1.2:1.

Boric acid in solid form or aqueous solutions of boric acid can be used. When aqueous solutions of boric acid are used, the water is subsequently removed by distillation. Preferably, the mole ratio of boric acid to tungstate salt is in the range of about 2:1 to about 20:1. More preferably, the mole ratio of boric acid to tungstate salt is in the range of about 15:1 to about 20:1.

The alkanediol employed in making the boron-modified catalysts can be a straight-chain or branched chain compound. Preferably, but not necessarily, at least one of the hydroxyl groups is on a terminal carbon atom. A few non-limiting examples of suitable diols include 2,3-butanediol, 2,4-pentanediol, 1,3-propanediol, 1,3-butanediol, and 2-methyl-1,3-propanediol. More preferred are 1,2-alkanediols which can be a straight-chain diol or a branched 1,2-diol, with the straight-chain 1,2-diols being more preferred. Regardless of its structure, the alkanediol preferably contains about 3 to about 12 carbon atoms, more preferably in the range of about 5 to about 10 carbon atoms, and still more preferably in the range of 5 to 8 carbon atoms. Non-limiting examples of suitable preferred 1,2-alkanediols include 1,2-propanediol, 2-methyl-1,2-propanediol, 1,2-butanediol, 1,2-pentanediol, 4-methyl-1,2-pentanediol, 1,2-hexanediol, 3-ethyl-1,2-hexanediol, 1,2-heptanediol, 1,2- octanediol, 1,2-nonanediol, 1,2-dodecanediol, and the like. More preferred diols are 1,2-pentanediol, 1,2-hexanediol, 1,2-heptanediol, and 1,2-octanediol, and of which 1,2-hexanediol is especially preferred. It is also preferred to select the diol that corresponds to the 1-alkene chosen; e.g., if 1-hexene is the 1-alkene, the most preferred diol is 1,2-hexanediol. This eases the workup done after the epoxidation reaction has been performed. Although not preferred, mixtures of diols may be used in the epoxidation reaction. The mole ratio of 1,2-alkanediol to tungstate salt is preferably in the range of about 15:1 to about 30:1.

Hydrogen peroxide used to make the preformed catalyst solution may be neat or an aqueous solution. Again, aqueous solutions are preferred for safety reasons. The concentration of hydrogen peroxide in the aqueous solution is preferably in the range of about 30 wt % to about 80 wt %; and more preferably in the range about 50 wt % to about 75 wt %. Concentrations of hydrogen peroxide toward the higher end of the range, i.e., closer to 75 wt %, e.g., about 70 wt %, are highly preferred.

In forming the boron-modified catalysts and carrying out the epoxidation, boric acid and diol can be mixed together with quaternary ammonium salt, the preformed catalyst solution and the 1-alkene in any order.

Without wishing to be bound by theory, and as noted above, it is believed that contacting the components of the preformed catalyst solution produces a peroxotungstate compound, which acts as a catalyst for the formation of the epoxide.

Various epoxidizable olefinic compounds can be epoxidized and purified in the practice of this invention. Preferred however are 1-alkene hydrocarbons. These can be a straight-chain 1-alkene or a branched 1-alkene; straight-chain alkenes are preferred. The alkene typically contains 2 to about 12 carbon atoms, but can contain even more carbon atoms. Suitable alkenes include ethylene, 1-propene, 2-methyl-1-propene, 1-butene, 1-pentene, 4-methyl-1-pentene, 1-hexene, 3-ethyl-1-hexene, 4-n-propyl-1-heptene, 1-octene, 1-nonene, 1-unadecene, 1-dodecene, 5-methyl-1-dodecene, 1-tetradecene, 1-hexadecene, and the like. Preferred alkenes are 1-pentene, 1-hexene, 1-heptene, and 1-octene; highly preferred is 1-hexene. Though not preferred, mixtures of alkenes may be used in the practice of this invention. The possibility of epoxidizing and purifying aromatic or cycloaliphatic hydrocarbons containing one or more epoxidizable olefinic ring substituents, dienes, and/or functionally-substituted olefins using the catalysts of this invention has not escaped our attention, and is deemed entirely feasible. Examples of aromatic or cycloaliphatic hydrocarbons containing one or more epoxidizable olefinic ring substituents include styrene, divinylbenzene, and vinylcyclohexane. Such compounds as 1,4-pentadiene, 1,5-hexadiene, 3,7-dimethyl-1,6-octadiene, and 7-methyl-2,4-octadiene serve as examples of epoxidizable dienes. Examples of functionally-substituted olefinic compounds are given in some of the references incorporated herein by reference, as well as in other references in the prior art.

In conducting the epoxidation, hydrogen peroxide may be used neat or as an aqueous solution. For safety reasons, it is preferred to use an aqueous solution of hydrogen peroxide. The concentration of hydrogen peroxide in the aqueous solution is preferably in the range of about 30 wt % to about 75 wt %; and more preferably in the range about 50 wt % to about 70 wt %. Such higher concentrations of hydrogen peroxide are preferred because they minimize the amount of water introduced to the reaction mixture.

Water is present in the epoxidation reaction as a reaction product, and is also introduced with hydrogen peroxide and the preformed catalyst solution. Because a single, predominantly organic phase is desired for the epoxidation reaction, water is removed during the reaction. This is preferably done by distillation. Removal of the water minimizes undesired side reactions.

A more preferred mode of operation is the mixing of all of the components except the hydrogen peroxide, heating the mixed components to reflux, and then mixing the hydrogen peroxide; more highly preferred is the continuing of reflux conditions during the entire mixing of the hydrogen peroxide. A highly preferred way of operating is to mix the alkene and ammonium salt; mix this with the preformed catalyst solution and boric acid; heat this latter mixture to reflux; and then mix the hydrogen peroxide while maintaining reflux conditions. It is also preferred to remove the produced epoxide, preferably by distillation.

The epoxidation reaction can be, and preferably is, conducted in continuous mode. It is preferred to conduct the process so that the volume of the contents of the reactor and the volume of the portion of the reaction product removed from the reactor are equal or substantially equal whereby the volume of reactor contents remains constant or substantially constant. In this way, reactors with smaller volumes can be employed. Thus, once steady-state conditions have been achieved in a continuous reactor, the separate feeds can be fed in appropriate proportions on a continuous basis, and the reactor contents maintained under the appropriate reaction conditions for virtually unlimited periods of time. Additionally, the per catalyst use can be maximized, in the sense that replacement catalyst solution need not be added until that already present in the reaction zone shows signs of degradation.

When a continuous process is started, the preformed catalyst solution and the quaternary ammonium salt and the boric acid and 1,2-diol and some 1-alkene are present in the reaction zone prior to initiating feeding of the hydrogen peroxide and 1-alkene. It is also preferred that the hydrogen peroxide and 1-alkene are fed concurrently. If the amount of one feed or the other is greater, the reaction will not be adversely affected, nor will the degradation of the catalyst be accelerated.

During all or substantially all of the time that both the 1-alkene and the hydrogen peroxide are being fed, reflux conditions are maintained in the reaction zone. Both water and the epoxide that is formed are removed from the reaction zone during the epoxidation reaction; both are preferably removed by distillation. Because water is continually formed during the epoxidation reaction, continuous or substantially continuous removal of the water from the reaction zone is necessary in order to maintain a single, predominantly organic phase in the reaction zone. The epoxide is preferably removed continuously or substantially continuously from the reaction zone.

In order to operate in continuous mode for long periods of time, the catalyst occasionally needs to be replenished. This is easily and preferably accomplished by intermittently adding more of the preformed catalyst solution to the reaction zone.

The epoxidation reactions, whether performed in a batch mode, semi-batch mode, or continuous mode, are preferably conducted so that such things as the feeds, reaction, and maintenance of reflux conditions occur"continuously" during the reaction. However, it cannot be stressed strongly enough that one must not gain the impression that inconsequential interruption in one or more of such things cannot occur. Interruptions which do not materially affect the conduct of the process are not excluded from the scope of this invention. To safeguard against hypertechnical legalistic word interpretation, it has been deemed prudent to employ terms such as "substantially continuously" in describing this invention. But whatever the terms used, the process should be conducted as one of ordinary skill in the art would carry out the processes after a thorough, unbiased reading of this entire disclosure and in keeping with the spirit of the description gained from such a reading.

The use of the term "concurrent" does not exclude the possibility of inconsequential interruptions taking place during the feeds. Nor does this term imply that the feeds must start at exactly the same moment in time. In the case of a co-feed process, the two feeds can be initiated with an interval of time between such initiation as long as the interval is sufficiently short as to cause no material adverse effect upon the overall process. Likewise in the case of a tri-feed or multi-feed operation, there may be one or two different time intervals between or among the respective feeds, again provided that the time intervals are of sufficiently short duration to cause no material adverse effect upon the overall process.

For a batch run or for an initial charge to a reaction zone in a continuous process, the mole ratio of ammonium salt to 1-alkene is preferably in the range of about 1:500 to about 1:1500, and more preferably is in the range of about 1:800 to about 1:1000. In a continuous process, when the quaternary ammonium salt needs to be replenished, due to decomposition in the reactor, the ammonium salt can be mixed with the alkene or can be intermittently added with the preformed catalyst solution, such that the optimal catalytic activity and selectivity are maintained.

While the use of equimolar or nearly equimolar amounts of 1-alkene or hydrogen peroxide may be desirable, either the 1-alkene or the hydrogen peroxide can be used as the reagent in excess without adverse effect on the process.

The practice and advantages of this invention are illustrated by the following Examples which are not intended to limit, and which should not be construed as limiting, the present invention to the specific operations described therein. In Examples 3–5, 1,2-hexanediol is produced by hydrolysis from 1,2-epoxyhexane which in turn was produced in Example 1 by oxidation of 1-hexene with hydrogen peroxide using a peroxotungstate catalyst. The 1,2-epoxyhexane crude was found to contain impurities of aldehydes, ketones, and organic acids which, if not removed, would contribute unacceptable odor to the 1,2-hexanediol product. This problem was overcome pursuant to this invention treating the crude 1,2-epoxyhexane with sodium borohydride in caustic solution prior to the hydrolysis reaction of 1,2-epoxyhexane to 1,2-hexanediol. The odor of the final 1,2-hexanediol product is greatly reduced. Comparative Example 2 shows that when sodium borohydride was not included in the aqueous alkaline wash, the odor in the final 1,2-hexanediol product was unacceptable.

Example 1 illustrates a preferred general method for producing 1,2-epoxyalkanes on a continuous basis.

EXAMPLE 1

Production of 1,2-Epoxyhexane

Figure 1:
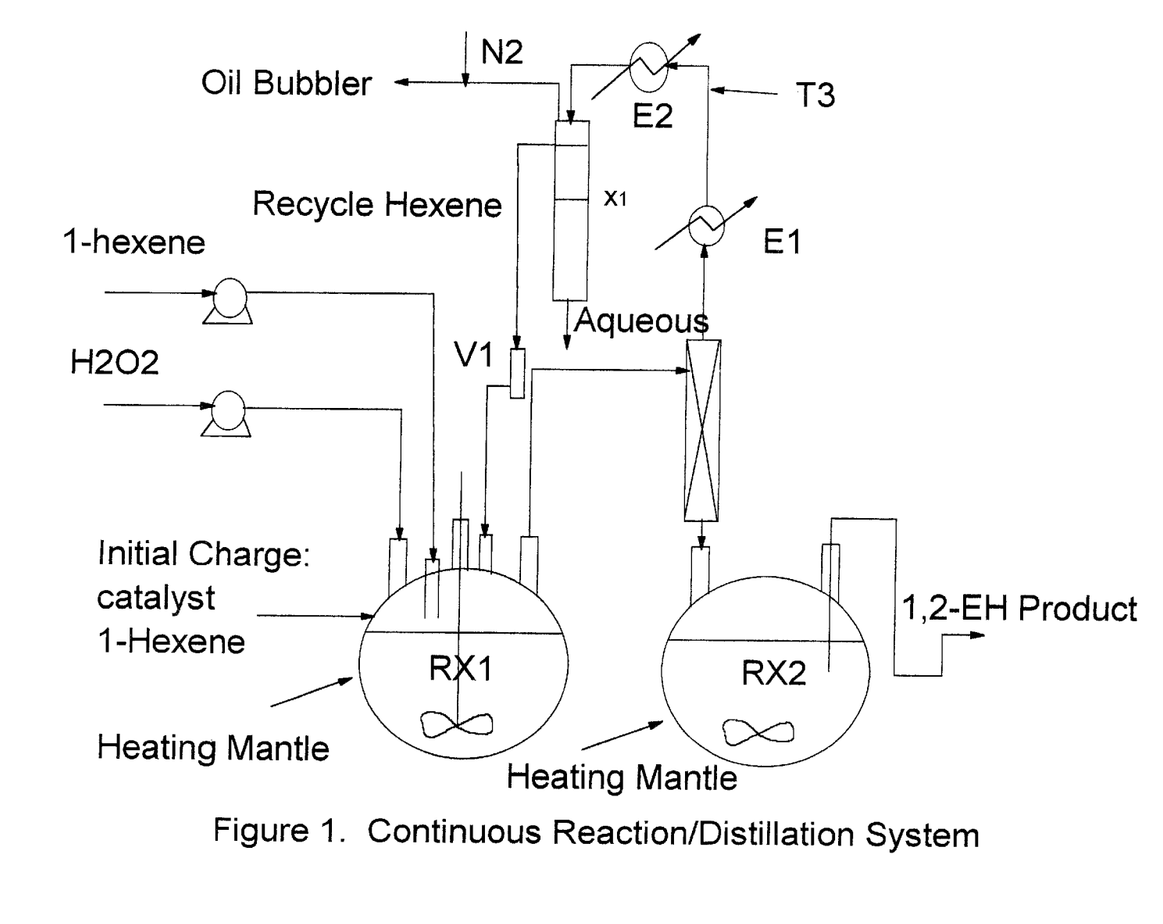
FIG. 1 schematically depicts preferred apparatus for producing a vicinal epoxide such as 1,2-epoxyhexane in a continuous process on a laboratory scale.

A schematic diagram of the continuous reaction system used is given in FIG. 1. 1-Hexene and 70% $H_2O_2$ were continuously fed to the epoxidation reactor (RX1), a 500-mL round bottom pyrex flask. The vapor stream from RX1 was continuously distilled using a 1.25-inch OD and 11-inch long column packed with stainless steel Pro-Pak® packing. The column allowed the continuous separation and removal of the 1,2-epoxyhexane product from the water by-product and recycle 1-hexene. In a typical operation, a peroxotungstate solution is prepared by stirring a mixture of 4.234 g of 34.89% $Na_2WO_4.2H_2O$ in water, 0.623 g of 96.4% $H_2SO_4$, and 1.444 g of 70% $H_2O_2$. RX1 is initially charged with a solution of 1.80 g of Aliquat® 336, Aldrich Chemical Company) and 287.9 g of 1-hexene (98%), 7.50 g of 1,2-hexanediol, and 3.94 g boric acid. The column reboiler (RX2) is charged with 61.5 g of 1-hexene. RX1 and RX2 are then heated until boiling. The overhead distillate temperature (T3) was maintained at ~63° C. by an air-cooled partial condenser (E1). The condensate from the overhead total condenser (E2) is fed to a phase separator (X1). The top 1-hexene phase from X1 is continuously overflowed to a 25-mL volumetric flask (VI) and then recycled directly back to RX1. The heat inputrate to RX1 is adjusted such that the hexene recycle flow rate is about 5 cc/min. The heat input rate to RX2 is adjusted to maintain a roughly constant level in RX2.

After conditions stabilized, 5.69 g of the above peroxotungstate solution (4.04 mmol of W) is added slowly to the reactor. Then 2.1 g of 70% $H_2O_2$ is fed to RX1 via a peristaltic pump over 25 minutes. The peroxide flow rate is then maintained at ~10.7 g/hr. The aqueous level in X1 is maintained at about 20 mL by continuously purging the aqueous layer to a 25-mL graduater. The $H_2O_2$ level in the aqueous layer is measured by titration with $Na_2S_2O_5$ and with the use of Quantofix peroxide test strips (Aldrich).

Both RX1 and RX2 temperatures start to increase as 1,2-epoxyhexane is formed. When RX2 temperature reaches 121° C., 1-hexene is feed continuously to RX1. The flow rate is adjusted slightly during the reaction to maintain roughly constant liquid volume in RX1. The liquid level in RX2 is maintained roughly constant (~80 g) by continuously purging to the 1,2-epoxyhexane product receiver (P1).

The catalytic selectivity and reactivity are continuously monitored by analyzing samples from RX1, RX2, and the aqueous byproducts. The deactivation of the catalyst is indicated by an increase in the H202 level in the aqueous phase. The reaction proceeds without any observable catalyst deactivation until after about 61 hours when the amount of 1,2-epoxyhexane made starts decreasing. 0.67 G of 34.9% $Na_2WO_4.2H_2O$ was added to the reactor at 64 hours. However, the rate of 1,2-epoxyhexane is not restored completely. The reaction is allowed to continue for a total of 68 hours.

A total of 710.9 g of 70% $H_2O_2$ (14.6 gmol) and 1030.3 g of 1-hexene (12.3 gmol) are fed. The final reaction heel in RX1 contains 48 wt % of 1-hexene, 16 wt % of 1,2-epoxyhexane. A total of 12.1 gmol 1,2-epoxyhexane is produced. The overall 1,2-epoxyhexane yield after 68 hours, based on the $H_2O_2$ charged, is calculated to be 83%.

The 1,2-epoxyhexane crude produced in Example 1 was used in Examples 2–5 below. This 1,2-epoxyhexane crude when analyzed by GC was found to contain 96.6% 1,2-epoxyhexane, 0.4% 1-hexene, 0.2% pentanal, 0.5% 1-hydroxy-2-hexanone, and 0.2% pentanoic acid.

EXAMPLE 2 (COMPARATIVE)

Synthesis of 1,2-Hexanediol (1,2-HD)-1,2-Epoxyhexane (1,2-EH) Washed with Caustic Only Part (a). Caustic and Water Washes 318.0 Grams of 1,2-EH was added to a 500-mL separatory funnel. 31.8 Grams of 10% caustic was charged to the funnel and mixed well for 5 min. The mixture was settled for approximately 20 min and phase separated. The bottom aqueous phase weighed 30.9 g (yellow), and the top organic phase weighed 318.8 g. The organic phase was then washed twice with tap water (31.8 g each). The washed 1,2-EH weighed 316.5 g and contained 96.8% 1,2-EH, 0.3% 1-hexene, and 0.2% pentanal.

Part (b). Batch Hydrolysis Reaction Catalyzed by Sodium Bicarbonate ($NaHCO_3$)

400 Grams of water and 8.00 g of $Na_2HCO_3$ were charged to a 1 liter stainless steel autoclave reactor, equipped with an electrical concentric furnace, thermowell, mechanical agitator, pressure transmitter, and a cooling coil. After pressure testing with nitrogen and venting to atmospheric pressure, the reactor was then heated to and maintained at 152° C. During heating, the reactor was periodically vented to remove the inerts. 151.1 g of 1,2-EH from Part (a) was then fed at a constant rate to the reactor via a dipleg over 3 hours and then the reactor was allowed to cook for an additional 30 mins. The reactor pressure peaked at about 69 psig after about 30 mins of feeding 1,2-EH but then slowly dropped to 55 psig at the completion of the reaction. The reaction mass (550.9 g) was analyzed by gas chromatography and contained 31% 1,2-HD, 0.3% 1,2-EH, and 1.2% dimer.

Part (c). Water/HD Distillation

A batch distillation column packed with 12-inch glass Raschig Rings and equipped with a round bottom flask and an overhead condenser was used. To the bottom flask was charged with 544.2 g of the hydrolysis reaction crude from Part (b). 372.9 Grams of water containing 2.8% of 1,2-HD was first distilled at 100 mmHga and until the bottom temperature reached 150° C. 1,2-HD was then recovered in the distillate at 35 mmHga. The bottom temperature increased slowly from about 147° C. to 170° C. The 1,2-HD (142.3 g) was analyzed by GC and contained 98.9% 1,2-HD, 0.1% dimers, 27 ppm pentanal, 4.8 ppm hexanal, and 350 ppm 1,2-EH.

Part (d). Nitrogen Stripping

Figure 3:
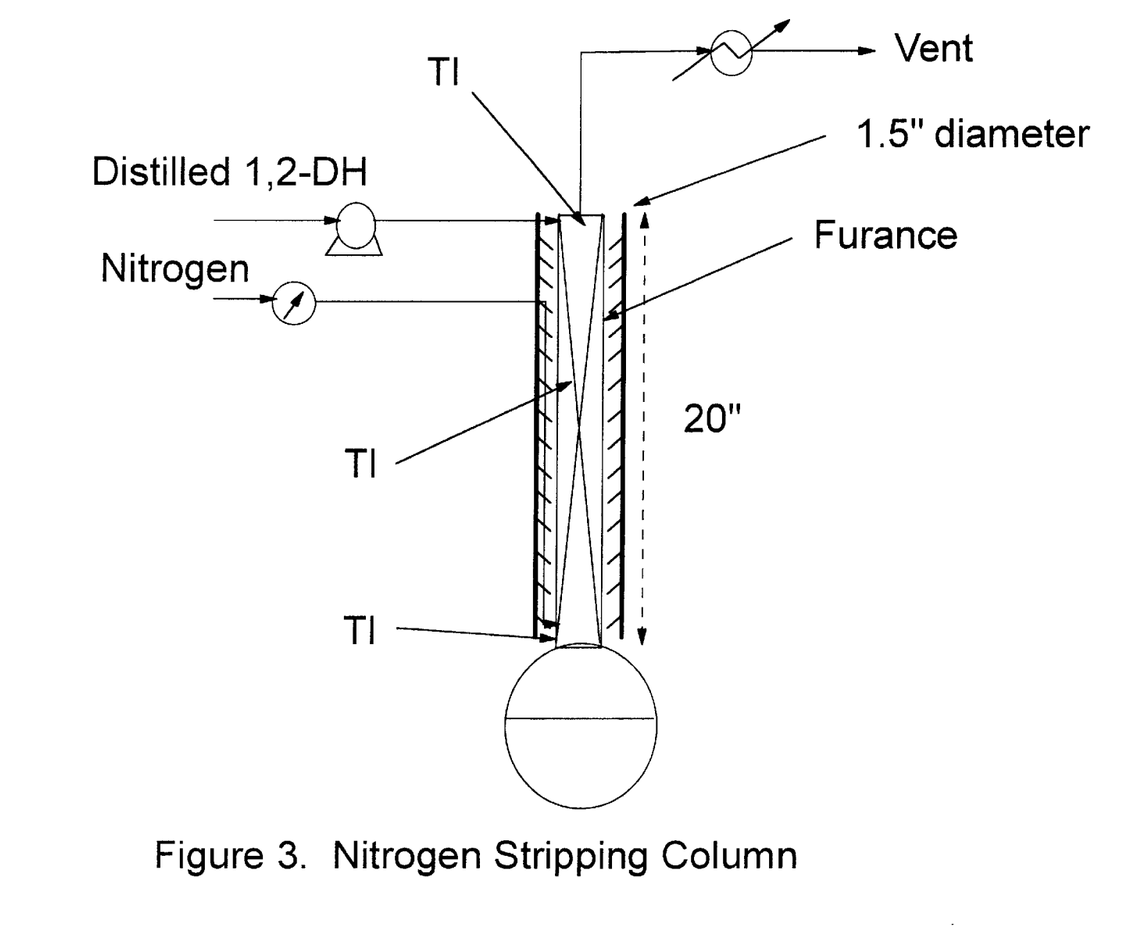
FIG. 3 schematically depicts preferred apparatus including a nitrogen stripping column for still further purifying vicinal alkanediol such as 1,2-hexanediol on a laboratory scale.

A schematic diagram of the nitrogen stripping setup is shown in FIG. 4. The column was a 20-inch long 1.5-inch OD Pyrex column packed with ¼-inch SS ProPak® packing. The bottom 1-foot section was heated by a concentric electrical furnace maintained at 131° C. while the top 8-inch section was heated by an electrical heating tape maintained at a surface temperature of about 145° C. Thermocouples were placed in the top, middle, and bottom of the column and typically read 100–135° C. during operation. 1,2-HD was fed to the top of the column using a Masterflex peristaltic pump at a constant rate of about 4.0 g/min. Nitrogen, maintained at 0.44 scfh by a rotameter, was preheated by the electrical furnace and fed to the bottom of the column. The liquid effluent was collected in the bottom of the column into a RB flask. The vapor stream was cooled by a water-cooled condenser. After feeding, the column was allowed to drain for about 10 mins. However, typically about 10–20 g of the 1,2-HD remained in the column internals. The overhead distillate typically weighed 2–4% of the 1,2-HD fed. Although it may not be necessary, all 1,2-HD samples prepared in this work were passed to the column twice.

140 Grams of the 1,2-HD distillate from Part (c) was processed with this nitrogen stripping column. 115 Grams of final 1,2-HD product was obtained and was found by GC to contain 99.2% 1,2-HD, 0.1% dimer, 7 ppm pentanal, 0.7 ppm hexanal, and 2.2 ppm 1,2-EH. The sample has a grassy odor and failed the odor specification of a company using 1,2-HD in its commercial operations.

EXAMPLE 3

Treatment of 1,2-EH and Synthesis of Low-Odor 1, 2-HD Pursuant to this Invention Part (a). $NaBH_4$/Caustic Wash 149.0 Grams of the above 1,2-EH was mixed with 3.77 g of 12% $NaBH_4$ in 40% caustic and 11.5 g of water for 30 mins at ambient temperature. The top organic phase was then washed twice with 15.7 g of water. The washed 1,2-EH was analyzed by GC and found to contain 97.1% 1,2-EH, 0.4% 1,2-HD, and 0.3% 1-hexene.

Part (b). Batch Hydrolysis Reaction Catalyzed by Sodium Bicarbonate

The hydrolysis reaction was conducted in the same manner as in Part (b) of Comparative Example 2, except that 388 g of water and 7.76 g of $NaHCO_3$ were initially charged to the reaction, and 145.1 g of 1,2-EH from Part (a) of the present Example was fed to the reactor over 2.4 hrs. The reaction mass (536.5 g) was analyzed by GC and found to contain 29.6% 1,2-HD, 0.7% dimer, and 0.6% 1,2-EH.

Part (c). Water/HD Distillation

The same procedure and equipment as in Part (c) of Comparative Example 2 were used. 532.1 Grams of the hydrolysis crude from Part (b) of the present Example was charged. The first distillate cut (360.3 g) contained 0.3% 1,2-EH and 0.8% 1,2-HD. The second distillate cut (146.7 g) contained 99.0% 1,2-HD, 0.1% dimers, 3.1 ppm pentanal, 2.6 ppm hexanal, and 75.1 ppm 1,2-EH. The residual bottom material (12.9 g) was extracted with 107.9 g water. The bottom aqueous phase (110.4 g) was analyzed by GC and contained 0.1% 1,2-HD. The top organic phase (9.2 g) contained 1.2% 1,2-HD and 92.9% dimers.

Part (d). Nitrogen Stripping

The same procedure and equipment as in Part (d) of Comparative Example 2 were used. A total of 145.1 g of 1,2-HD from Part (d) of the present Example was fed. 113.2 Grams of final product was obtained and contained by GC analysis 99.1% 1,2-HD, 0.1% dimer, 0.6 ppm pentanal, 0.5 ppm hexanal, and 2.3 ppm 1,2 EH. This sample passed the above commercial minimum odor specification.

EXAMPLE 4

Treatment of 1,2-EH and Synthesis of Low-Odor 1, 2-HD Pursuant to this Invention Part (a). $NaBH_4$/Caustic Wash 154.3 Grams of the above 1,2-EH was first slowly added with 1.938 g of 12% $NaBH_4$ in 40% caustic and 13.4.5 g of water at ambient temperature. The pentanal levels slowly dropped to about 0.024 GC area %. Then an additional 1.89 g of 12% $NaBH_4$ in 40% caustic solution was added. The top organic phase was then washed once with 15.7 g of water. The washed 1,2-EH was analyzed by GC and found to contain 96.7% 1,2-EH, 0.5% 1,2-HD, and 0.3% 1-hexene.

Part (b). Batch Hydrolysis Reaction Catalyzed by $NaHCO_3$

The hydrolysis reaction was conducted in the same manner as in Part (b) of Comparative Example 2, except that 400 g of water and 8.0 g $NaHCO_3$ were initially charged to the reaction and 148.6 g of 1,2-EH from Part (a) of the present Example was fed to the reactor over 2.5 hrs. The reaction mass (553.2 g) was analyzed by GC and found to contain 28.1% 1,2-HD, 1.3% dimer, and 0.3% 1,2-EH.

Part (c). Water/HD Distillation

The same procedure and equipment as in Part (c) of Comparative Example 2 were used. 528.9 Grams of the hydrolysis crude from Part (b) of the present Example was charged. The first distillate cut (363.1 g) contained 0.3% 1,2-EH and 0.5% 1,2-HD. The second distillate cut (146.8 g)

contained 98.0% 1,2-HD, 0.3% dimers, 2.1 ppm pentanal, 1.5 ppm hexanal, and 65.3 ppm 1,2-EH.

The residual bottom material (11.4 g) was extracted with 101.4 g water. The bottom aqueous phase (103.9 g) contained 0.04% 1,2-HD by GC while the top organic phase (7.3 g) contained 0.9% 1,2-HD and 92.2% dimers.

Part (d). Nitrogen Stripping

The same procedure and equipment as in Part (d) of Comparative Example 2 were used. A total of 144.6g of 1,2-HD from Part (d) of the present Example was fed. 116.4 Grams of final product was obtained and contained 98.2% 1,2-HD, 0.4% dimer, 1.0 ppm pentanal, 0.4 ppm hexanal, and 1.7 ppm 1,2 EH. This sample passed the above commercial odor specification.

EXAMPLE 5

Treatment of 1,2-EH and Synthesis of Low-Odor 1, 2-HD Pursuant to this Invention Part (a). NaBH$_4$/Caustic Wash 150.8 Grams of the above 1,2-EH was treated with 3.746 g of 12% NaBH$_4$ in 40% caustic and 12.27 g of water at 20–50° C. for 3.5 hours. The top organic phase was then washed once with 15.6 g of water. The washed 1,2-EH was analyzed by GC and contained 96.6% 1,2-EH, 0.5% 1,2-HD, and 0.3% 1-hexene.

Part (b). Batch Hydrolysis Reaction Catalyzed by Methanesulfonic Acid (CH$_3$SO$_3$H)

397.2 Grams of water and 0.40 g of CH$_3$SO$_3$H were charged to a 1-liter stainless steel autoclave reactor, equipped with an electrical concentric furnace, thermowell, mechanical agitator, pressure transmitter, and a cooling coil. After pressure testing with nitrogen and venting to atmospheric pressure, the reactor was then heated to and maintained at 124° C. During heating, the reactor was periodically vented to remove the inerts. 145.77 Grams of 1,2-EH from Part (a) of the present Example was then fed at a constant rate to the reactor via a dipleg over 55 mins and then the reactor was allowed to cook for an additional 5 mins. The reactor pressure peaked at about 24 psig after about 5 mins of feeding 1,2-EH but then slowly dropped to 19 psig at the completion of the reaction. The reaction mass (540 g) was analyzed by gas chromatography and was found to contain 28.5% 1,2-HD, 0.1% 1,2-EH, and 1.3% dimer.

Part (c). Water/HD Distillation

The same procedure and equipment as in Part (c) of Comparative Example 2 were used. 530.4 Grams of the hydrolysis crude from (b) of the present Example were neutralized to a pH value of 7.5 with 2.45 g of 2.5% caustic and then charged to the reactor. The first distillate cut (372 g) contained 0.1% 1,2-EH, 0.5% 1,2-HD, and 0.1% dimers. The second distillate cut (144.5 g) contained 97.7% 1,2-HD and 0.2% dimers. The residual bottom material (13.1 g) contained 2.8% 1,2-HD and 86.3% dimers.

Part (d). Nitrogen Stripping

The same procedure and equipment as in Part (d) of Comparative Example 2 were used. A total of 143.6 g of 1,2-HD from Part (c) of the present Example was fed. 113.3 Grams of final product was obtained and contained 98.4% 1,2-HD, 0.4% dimer, 1.0 ppm pentanal, 0.4 ppm hexanal, and 1.7 ppm 1,2 EH. This sample also passed the above commercial odor specification.

Example 6 illustrates methods of producing epoxyalkanes in batch-type operations. The product mixtures can be purified as in Examples 3–5.

EXAMPLE 6

Figure 2:
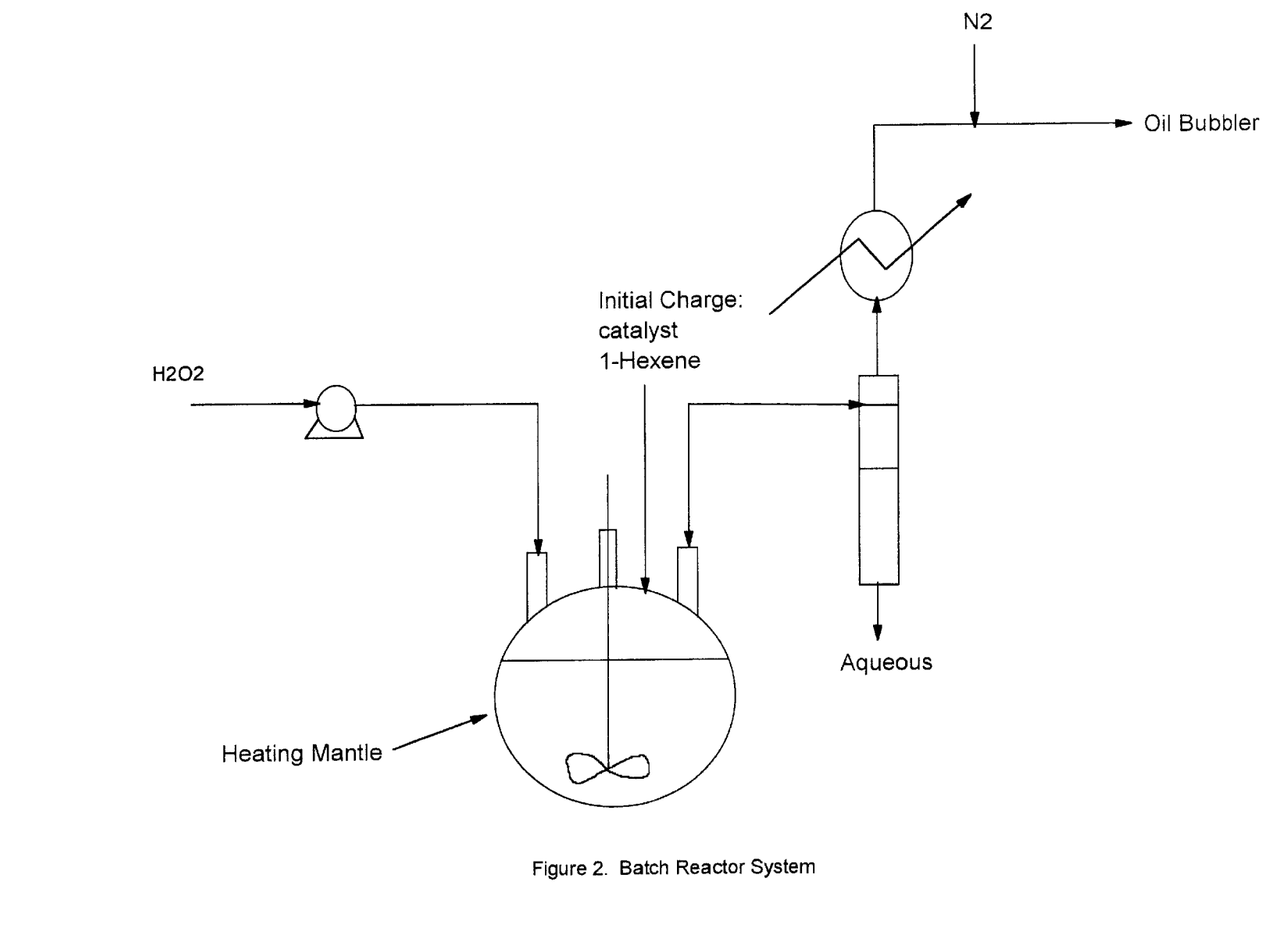
FIG. 2 schematically depicts preferred apparatus for producing a vicinal epoxide such as 1,2-epoxyhexane in a batch process on a laboratory scale.

Apparatus used in this operation is schematically illustrated in FIG. 2. To a 500-mL Pyrex reactor are first charged a mixture of 1.27 g tricaprylylmethylammonium chloride (2.6 mmol; Aliquat® 336, Aldrich Chemical Company) and 210.2 g 1-hexene (2,498 mmol). 1,2-Hexanediol and boric acid are initially added when the Aliquat product and 1-hexene solution are added to the reactor. The reactor is then heated, reaching reflux temperature (~64° C.) within about 30 minutes. A peroxotungstate solution is prepared by mixing 34.9 wt % Na$_2$WO$_4$.2H$_2$O (2.708 g, 2.86 mmol W), 96.4% H$_2$SO$_4$ (0.398 g, 3.91 mmol), and 70% H$_2$O$_2$ (0.90 g, 18.5 mmol) for about 2 minutes at room temperature, resulting in a clear peroxotungstate solution. The peroxotungstate solution is then added to the reactor during 11 minutes via a dropping funnel. Following the addition of the peroxotungstate solution, 70% H$_2$O$_2$ is fed to the reactor over a period of several hours. The peroxide flow rate is slower (~half of the full rate) in the first 30 minutes and maintained at a constant rate afterward. Throughout the reaction, reflux conditions are maintained.

The byproduct water is continuously removed from the reactor by azeotropic distillation to ensure that a single, organic phase was present in the reactor. The aqueous phase is collected in a Dean-Stark trap while the organic phase is continuously refluxed back into the reactor. During such operation, oxygen evolution was observed in the oil bubbler. Based on the bubbling rate, it was estimated that 5–10% of the peroxide decomposed to oxygen. The rate of peroxide decomposition was much higher during the first 2 hours. The reaction is stopped after all of the peroxide has been fed and the reactor had been heated for an additional 10 minutes. When a top organic phase was present in the Dean-Stark trap, that organic phase was combined with the reaction mass. The organic reaction mass was analyzed by gas chromatography for 1-hexene and 1,2-epoxyhexane. A sample of the reaction mass was extracted with 10 × deionized water and the pH of the extract was measured using a pH probe. The pH of the final mixtures ranged from 3.3 to 4.1. The aqueous phase was collected from the Dean-Stark trap and its H$_2$O$_2$ concentration was determined by titration with Na$_2$S$_2$O$_5$ and by using Quantofix H$_2$O$_2$ test strips (Aldrich Chemical Company). It was assumed that one mole of Na$_2$S$_2$O$_5$ can destroy two moles of H$_2$O$_2$.

All of the batch runs used the same amounts of Na$_2$WO$_4$, H$_2$SO$_4$, and 1-hexene. The amounts of 1,2-hexanediol, boric acid, and 70% H$_2$O$_2$ employed in each run are given in Table 2. The 1,2-epoxyhexane yield is based on the total amount of hydrogen peroxide charged.

TABLE 2

| Run | 1,2-hexanediol (mmol) | B(OH)$_3$ (mmol) | H$_2$O$_2$ Fed (mmol) | H$_2$O$_2$ Feed Time | H$_2$O$_2$ Decomposed | Yield |
| --- | --- | --- | --- | --- | --- | --- |
| 1 | 45 | 45 | 1295 | 7.4 hr. | <2% | 89% |
| 2 | 46 | 24 | 289 | 7.3 hr. | <2% | 87% |
| 3 | 8.5 | 8.74 | 1274 | 7.2 hr. | | 70% |
| 4 | 21 | 10.7 | 1298 | 7.0 hr. | | 69% |
| 5 | 84 | 43 | 1270 | 7.2 hr. | <2% | 88% |
| 6 | 81 | 51.6 | 1118 | 7.0 hr. | | 80% |
| 7 | 46 | 45.8 | 1240 | 8.0 hr. | | 84% |

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any take place in the resulting mixture or solution or reaction medium as such changes, transformations and/or reactions are the natural result of bringing the specified reactants and/or components together under the conditions called for pursuant to this disclosure. Thus the reactants and other materials are identified as reactants and components to be brought together in connection with performing a desired chemical reaction or in forming a mixture to be used in conducting a desired reaction. Accordingly, even though the claims hereinafter may refer to substances, components and/or ingredients in the present tense ("comprises","is", etc.), the reference is to the substance, component, or ingredient as it existed at the time just before it was first contacted, blended or mixed with one or more other substances, components, or ingredients in accordance with the present disclosure. The fact that the substance, component, or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to a substance, component, or ingredient by chemical name or formula exclude the possibility that during the desired reaction itself a substance, component, or ingredient becomes transformed to one or more transitory intermediates that actually enter into or otherwise participate in the reaction. In short, no representation is made or is to be inferred that the named substances, components, or ingredients must participate in the reaction while in their original chemical composition, structure or form.

It will also be understood that such terms as "substantially" and "essentially" denote that the subject matter referred to need not involve absolutes. For example, instead of describing a variable operation such as removing water or feeding something"continuously", it is at least equally realistic to describe the operation as being conducted "substantially continuously", in as much as in practicing this invention it normally makes little, if any, difference if the operation is temporarily interrupted for a short period of time that does not do material harm to the process. It is equally realistic to specify that something is done "substantially the entire time" while something else is taking place, as slight interruptions or discontinuities in such things normally will make no material difference in the end result. In short, mathematical precision is not necessary under normal circumstances, and it would be absurd to suggest otherwise. Similarly, it is equally satisfactory to have a liquid phase either as "a single liquid phase" or as "an essentially single liquid phase". A little cloudiness or an insignificant amount of another liquid phase in most cases will cause no trouble and thus is acceptable. Since the words "essentially" and "substantially" are words in common usage and that are well-defined in the dictionary, they are deemed sufficiently precise and are thus used herein.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of treating at least one epoxyalkane, which process comprises subjecting the epoxyalkane(s) to at least one of the following washing operations:
   (i) washing the epoxyalkane(s) at least once with an aqueous washing solution of inorganic base, and then washing the epoxyalkane(s) at least once with an aqueous washing solution of borohydride; or
   (ii) washing the epoxyalkane(s) at least once with an aqueous washing solution of borohydride, and then washing the epoxyalkane(s) at least once with an aqueous washing solution of inorganic base; or
   (iii) washing the epoxyalkane(s) at least once with an aqueous washing solution of both inorganic base and borohydride;
such that undesirable odor is reduced or eliminated from alkanediol(s), if produced from the treated epoxyalkane(s) by hydrolysis.

2. A process as in claim 1 further comprising separating the epoxyalkane(s) from the aqueous washing solution or solutions used.

3. A process as in claim 2 further comprising hydrolyzing at least a portion of the separated epoxyalkane(s) to form one or more alkanediols.

4. A process as in claim 2 further comprising washing the separated epoxyalkane(s) with water.

5. A process as in claim 4 further comprising hydrolyzing at least a portion of the epoxyalkane(s) that has been or have been washed with water to form one or more alkanediols.

6. A process as in any of claims 1–5 wherein the epoxyalkane(s) is/are one or more 1,2-epoxyalkanes having in the range of 5 to about 8 carbon atoms per molecule.

7. A process as in claim 6 wherein the borohydride in (i), (ii), or (iii) is sodium borohydride and wherein the inorganic base in (i), (ii), or (iii) is sodium hydroxide.

8. A process as in any of claims 1–5 wherein the washing operation used is the washing operation of (iii).

9. A process as in claim 8 wherein the epoxyalkane(s) is/are one or more 1,2-epoxyalkanes having in the range of 5 to about 8 carbon atoms per molecule.

10. A process as in claim 9 wherein the borohydride is sodium borohydride and wherein the inorganic base sodium hydroxide.

11. A process for producing one or more alkanediols with reduced or eliminated undesirable odor or odor-causing impurities, which process comprises:
    a) conducting at least one of the following washing operations on at least one epoxyalkane:
       (i) washing the epoxyalkane(s) at least once with an aqueous washing solution of inorganic base, and then washing the epoxyalkane(s) at least once with an aqueous washing solution of borohydride; or
       (ii) washing the epoxyalkane(s) at least once with an aqueous washing solution of borohydride, and then washing the epoxyalkane(s) at least once with an aqueous washing solution of inorganic base; or
       (iii) washing the epoxyalkane(s) at least once with an aqueous washing solution of both inorganic base and borohydride; and
       separating the epoxyalkane(s) from the aqueous washing solution or solutions used; and
    b) hydrolyzing in the presence of acid or base at least one epoxyalkane from a) to form at least one alkanediol.

12. A process as in claim 11 wherein at least one alkanediol from said hydrolysis is recovered.

13. A process as in claim 11 wherein said hydrolysis is conducted in a continuous reactive distillation column from which column alkanediol with reduced or eliminated undesirable odor or odor-causing impurities is recovered.

14. A process as in any of claims 11–13 wherein the washing operation used is the washing operation of (iii).

15. A process as in any of claims 11–13 wherein the epoxyalkane(s) is/are one or more 1,2-epoxyalkanes having in the range of 5 to about 8 carbon atoms per molecule.

16. A process as in any of claim 15 wherein the borohydride is sodium borohydride and wherein the inorganic base sodium hydroxide.

17. A process for producing an alkanediol with reduced or eliminated undesirable odor or odor-causing impurities, which process comprises:
   a) conducting at least one of the following washing operations on at least one epoxyalkane:
      (i) washing the epoxyalkane(s) at least once with an aqueous washing solution of inorganic base, and then washing the epoxyalkane(s) at least once with an aqueous washing solution of borohydride; or
      (ii) washing the epoxyalkane(s) at least once with an aqueous washing solution of borohydride, and then washing the epoxyalkane(s) at least once with an aqueous washing solution of inorganic base; or
      (iii) washing the epoxyalkane(s) at least once with an aqueous washing solution of both inorganic base and borohydride; and
      separating the epoxyalkane(s) from the aqueous washing solution or solutions used;
   b) subjecting separated washed epoxyalkane(s) from a) to water washing, and separating the resultant water and washed epoxyalkane(s) from each other; and
   c) hydrolyzing in the presence of acid or base one or more washed epoxyalkane(s) from b) to form one or more alkanediols.

18. A process as in claim 17 wherein one or more alkanediols from the hydrolysis in c) is recovered.

19. A process as in claim 17 wherein the hydrolysis in c) is conducted in a continuous reactive distillation column from which column one or more alkanediols with reduced or eliminated undesirable odor or odor-causing impurities is recovered.

20. A process as in any of claims 17–19 wherein the washing operation used is the washing operation of (iii).

21. A process as in any of claims 17–19 wherein the epoxyalkane(s) is/are one or more 1,2-epoxyalkanes having in the range of 5 to about 8 carbon atoms per molecule.

22. A process as in claim 21 wherein the borohydride is sodium borohydride and wherein the inorganic base is sodium hydroxide.

23. A process of producing an alkanediol, which process comprises:
   A) epoxidizing in a liquid phase, an epoxidizable olefinic compound with hydrogen peroxide in the presence of a catalytic quantity of a tungsten-containing catalyst, to form an epoxide;
   B) conducting at least one of the following washing operations on said epoxide:
      (i) washing said epoxide at least once with an aqueous washing solution of inorganic base, and then washing said epoxide at least once with an aqueous washing solution of borohydride; or
      (ii) washing said epoxide at least once with an aqueous washing solution of borohydride, and then washing said epoxide at least once with an aqueous washing solution of inorganic base; or
      (iii) washing said epoxide at least once with an aqueous washing solution of both inorganic base and borohydride; and
      separating the epoxide from the aqueous washing solution or solutions used; and
   C) hydrolyzing in the presence of acid or base the epoxide from B) to form alkanediol.

24. A process as in claim 23 wherein (a) boric acid and (b) at least one alkanediol individually and/or as a reaction product of (a) and (b) are included in said liquid phase of A).

25. A process as in claim 23 wherein said tungsten-containing catalyst is a tungstate-containing catalyst.

26. A process as in claim 23 wherein at least one onium compound is included in said liquid phase of A).

27. A process as in claim 26 wherein said at least one onium compound is at least one quaternary ammonium compound.

28. A process as in claim 26 wherein said tungsten-containing catalyst system is a tungstate-containing catalyst.

29. A process as in claim 28 wherein said tungsten-containing catalyst is formed from components comprising (i) tungstic acid or a tungstate salt and an inorganic acid, and wherein said at least one onium compound is at least one quaternary ammonium compound in which each of three substituents on the nitrogen atom contains, independently, six to about sixteen carbon atoms, and the remaining substituent is methyl or ethyl.

30. A process according to claim 29 wherein said each of three substituents is an alkyl group, and wherein said remaining substituent is methyl.

31. A process as in any of claims 23–30 wherein said epoxyalkane is 1,2-epoxypentane, 1,2-epoxyhexane, 1,2-epoxyheptane, or 1,2-epoxyoctane, and wherein the washing operation used is (iii).

32. A process as in claim 31 wherein the 1,2-epoxyalkane is 1,2-epoxyhexane, and wherein the hydrolysis in C) is conducted in a continuous reactive distillation column from which column 1,2-hexanediol is recovered.

33. A process as in any of claims 23–30 further comprising washing the epoxyalkane with water after conducting B) and before conducting C).

34. A process of forming an epoxide, which process comprises:
   A) continuously or substantially continuously feeding aqueous hydrogen peroxide solution into a reaction mixture formed from components comprising at least one olefinic hydrocarbon to which have been added (i) tungstic acid and/or a tungsten compound, preferably a tungsten (VI) compound, and an inorganic acid, (ii) an onium compound, preferably a quaternary ammonium compound, (iii) boric acid and (iv) at least one alkanediol and/or (v) a borate ester-containing mixture formed from boric acid and at least one alkanediol;
   B) continuously or substantially continuously removing water from the reaction mixture by distillation so that at least during substantially the entire time the aqueous hydrogen peroxide is being fed, the reaction mixture has a liquid phase which is a single liquid phase or an essentially single liquid phase whereby an epoxide product is formed; and
   C) subjecting epoxide product from B) to at least one of the following washing operations:
      (i) washing the epoxide product at least once with an aqueous washing solution of inorganic base, and then washing the epoxide product at least once with an aqueous washing solution of borohydride; or (ii) washing the epoxide product at least once with an aqueous washing solution of borohydride, and then washing the epoxide product at least once with an aqueous washing solution of inorganic base; or (iii) washing the epoxide product at least once with an aqueous washing solution of both inorganic base and borohydride.

35. A process as in claim 34 wherein said olefinic hydrocarbon is at least one 1-alkene, and wherein said process further comprises recovering washed epoxide product from C) and hydrolyzing at least a portion of said epoxide product to form alkanediol.

36. A process of forming an epoxide, which process comprises:

A) continuously or substantially continuously cofeeding (1) aqueous hydrogen peroxide solution and (2) at least one olefinic hydrocarbon, into a reaction mixture formed from components comprising (a) at least one olefinic hydrocarbon (b) a tungsten compound, preferably (i) tungstic acid and/or (ii) a tungsten (VI) compound and an inorganic acid, (c) an onium compound, preferably a quaternary ammonium compound, and (d) boric acid and (e) at least one alkanediol and/or (f) a borate ester-containing mixture formed from boric acid and at least one alkanediol, such that at least one epoxide is continuously being formed;

B) continuously or substantially continuously removing water from the reaction mixture by distillation so that at least during substantially the entire time the aqueous hydrogen peroxide is being fed, the reaction mixture has a liquid phase which is a single liquid phase or an essentially single liquid phase whereby an epoxide product is formed; and C) subjecting epoxide product from B) to at least one of the following washing operations:
   (i) washing the epoxide product at least once with an aqueous washing solution of inorganic base, and then washing the epoxide product at least once with an aqueous washing solution of borohydride; or
   (ii) washing the epoxide product at least once with an aqueous washing solution of borohydride, and then washing the epoxide product at least once with an aqueous washing solution of inorganic base; or
   (iii) washing the epoxide product at least once with an aqueous washing solution of both inorganic base and borohydride.

37. A process as in claim 36 wherein said olefinic hydrocarbon is at least one 1-alkene, and wherein said process further comprises recovering washed epoxide product from C) and hydrolyzing at least a portion of said epoxide product to form alkanediol.

* * * * *